(12) United States Patent
Bolduc et al.

(10) Patent No.: US 9,848,869 B2
(45) Date of Patent: Dec. 26, 2017

(54) PROSTHESIS SYSTEMS AND METHODS

(75) Inventors: Lee Bolduc, Sunnyvale, CA (US); Juan Parodi, St. Louis, MO (US)

(73) Assignee: Medtronic Vascular, Inc., Minneapolis, MN (US)

( * ) Notice: Subject to any disclaimer, the term of this patent is extended or adjusted under 35 U.S.C. 154(b) by 1101 days.

(21) Appl. No.: 11/981,112

(22) Filed: Oct. 31, 2007

(65) Prior Publication Data

US 2008/0065191 A1 Mar. 13, 2008

Related U.S. Application Data

(60) Division of application No. 10/752,435, filed on Jan. 6, 2004, which is a continuation-in-part of application
(Continued)

(51) Int. Cl.
| | |
|---|---|
| *A61F 2/82* | (2013.01) |
| *A61B 17/064* | (2006.01) |
| *A61B 17/068* | (2006.01) |
| *A61F 2/07* | (2013.01) |
| *A61B 17/00* | (2006.01) |

(Continued)

(52) U.S. Cl.
CPC .......... *A61B 17/064* (2013.01); *A61B 17/068* (2013.01); *A61F 2/07* (2013.01); *A61B 2017/003* (2013.01); *A61B 2017/0646* (2013.01); *A61B 2017/0649* (2013.01); *A61F 2/064* (2013.01); *A61F 2/89* (2013.01); *A61F 2/90* (2013.01); *A61F 2002/065* (2013.01); *A61F 2002/067* (2013.01); *A61F 2002/075* (2013.01); *A61F 2250/0017* (2013.01); *A61F 2250/0023* (2013.01); *A61F 2250/0039* (2013.01)

(58) Field of Classification Search
CPC .......................................................... A61F 2/82
USPC ....................................................... 623/1.14
See application file for complete search history.

(56) References Cited

U.S. PATENT DOCUMENTS

| | | | |
|---|---|---|---|
| 2,033,039 | A | 3/1936 | Limpert |
| 3,499,222 | A | 3/1970 | Linkow et at. |

(Continued)

FOREIGN PATENT DOCUMENTS

| | | |
|---|---|---|
| AU | 2011224089 B2 | 7/2014 |
| EP | 0 321 912 | 12/1987 |

(Continued)

OTHER PUBLICATIONS

5mm Origin Tracker™ It Runs in Circles Around Staples, 1995 Advertising Literature.

(Continued)

*Primary Examiner* — Matthew Schall (57) ABSTRACT

Systems and methods for deploying a prosthesis in a tissue region in a hollow body organ or blood vessel provide a first prosthesis and a second prosthesis, each having a prosthetic material and a scaffold that supports the prosthetic material. The first prosthesis has a proximal neck region, and the second prosthesis has an end region. The end region is sized and configured to telescopically fit with the proximal neck region to form a composite prosthesis. The systems and methods manipulate a fastener attachment assembly to implant at least one fastener to secure the composite prosthesis in the tissue region.

14 Claims, 9 Drawing Sheets

Related U.S. Application Data

No. 10/693,255, filed on Oct. 24, 2003, now Pat. No. 6,929,661, which is a continuation-in-part of application No. 10/271,334, filed on Oct. 15, 2002, now Pat. No. 6,960,217.

(60) Provisional application No. 60/489,011, filed on Jul. 21, 2003, provisional application No. 60/333,937, filed on Nov. 28, 2001.

(51) Int. Cl.
*A61F 2/06* (2013.01)
*A61F 2/90* (2013.01)
*A61F 2/89* (2013.01)

(56) References Cited

U.S. PATENT DOCUMENTS

| | | |
|---|---|---|
| 3,686,740 A | 8/1972 | Shiley |
| 3,799,172 A | 3/1974 | Szpur |
| 4,140,126 A | 2/1979 | Choudhury |
| 4,255,820 A | 3/1981 | Rothermel et al. |
| 4,307,722 A | 12/1981 | Evans |
| 4,580,568 A | 4/1986 | Gianturco |
| 4,586,923 A | 5/1986 | Gould et al. |
| 4,625,597 A | 12/1986 | Cast |
| 4,781,682 A | 11/1988 | Patel |
| 4,898,577 A | 2/1990 | Badger et al. |
| 4,921,484 A | 5/1990 | Hillstead |
| 5,030,204 A | 7/1991 | Badger et al. |
| 5,042,707 A | 8/1991 | Taheri |
| 5,071,407 A | 12/1991 | Termin et al. |
| 5,104,399 A | 4/1992 | Lazarus |
| 5,199,950 A | 4/1993 | Schmitt et al. |
| 5,207,695 A | 5/1993 | Trout, III |
| 5,290,295 A | 3/1994 | Querals et al. |
| 5,320,630 A | 6/1994 | Ahmed |
| 5,330,490 A | 7/1994 | Wilk et al. |
| 5,330,503 A | 7/1994 | Yoon |
| 5,334,196 A | 8/1994 | Scott et al. |
| 5,456,714 A | 10/1995 | Owen |
| 5,470,337 A | 11/1995 | Moss |
| 5,480,382 A | 1/1996 | Hammerslag et al. |
| 5,489,295 A | 2/1996 | Piplani et al. |
| 5,522,881 A | 6/1996 | Lentz |
| 5,562,728 A | 10/1996 | Lazarus et al. |
| 5,571,171 A | 11/1996 | Barone et al. |
| 5,571,173 A | 11/1996 | Parodi |
| 5,582,616 A | 12/1996 | Bolduc et al. |
| 5,591,195 A | 1/1997 | Taheri et al. |
| 5,609,627 A | 3/1997 | Goicechea et al. |
| 5,626,613 A | 5/1997 | Schmieding |
| 5,639,278 A | 6/1997 | Dereume et al. |
| 5,662,683 A | 9/1997 | Kay |
| 5,662,700 A | 9/1997 | Lazarus |
| 5,676,696 A | 10/1997 | Marcade |
| 5,676,697 A | 10/1997 | McDonald |
| 5,700,269 A | 12/1997 | Pinchuk et al. |
| 5,702,365 A | 12/1997 | King |
| 5,713,907 A | 2/1998 | Hogendijk et al. |
| 5,769,884 A * | 6/1998 | Solovay .................. 623/1.13 |
| 5,779,731 A | 7/1998 | Leavitt |
| 5,810,882 A | 9/1998 | Bolduc et al. |
| 5,814,016 A | 9/1998 | Valley et al. |
| 5,824,008 A | 10/1998 | Bolduc et al. |
| 5,824,037 A | 10/1998 | Fogarty et al. |
| 5,824,041 A | 10/1998 | Lenker et al. |
| 5,855,565 A | 1/1999 | Bar-Cohen et al. |
| 5,855,598 A | 1/1999 | Pinchuk |
| 5,957,940 A | 9/1999 | Tanner et al. |
| 5,964,772 A | 10/1999 | Bolduc et al. |
| 5,968,053 A | 10/1999 | Revelas |
| 5,972,003 A | 10/1999 | Rousseau et al. |
| 5,972,023 A | 10/1999 | Tanner et al. |
| 5,980,548 A | 11/1999 | Evans et al. |
| 5,993,401 A | 11/1999 | Inbe et al. |
| 5,993,466 A | 11/1999 | Yoon |
| 6,070,589 A | 6/2000 | Keith et al. |
| 6,086,582 A | 7/2000 | Altman et al. |
| 6,090,137 A | 7/2000 | Schmitt |
| 6,126,685 A | 10/2000 | Lenker et al. |
| 6,145,509 A | 11/2000 | Tanner |
| 6,146,339 A | 11/2000 | Biagtan et al. |
| 6,217,597 B1 | 4/2001 | Tanner |
| 6,248,118 B1 | 6/2001 | Tanner et al. |
| 6,258,119 B1 | 7/2001 | Hussein et al. |
| 6,270,516 B1 | 8/2001 | Tanner et al. |
| 6,287,315 B1 | 9/2001 | Wijeratne et al. |
| 6,287,335 B1 | 9/2001 | Drasler et al. |
| 6,296,656 B1 | 10/2001 | Bolduc et al. |
| 6,302,906 B1 | 10/2001 | Goicoechea et al. |
| 6,336,933 B1 | 1/2002 | Parodi |
| 6,371,919 B1 | 4/2002 | Tanner et al. |
| 6,398,803 B1 | 6/2002 | Layne et al. |
| 6,409,757 B1 | 6/2002 | Trout, III et al. |
| 6,416,365 B1 | 7/2002 | Iwahori |
| 6,428,565 B1 | 8/2002 | Wisselink |
| 6,458,152 B1 | 10/2002 | Khosravi et al. |
| 6,520,974 B2 | 2/2003 | Tanner et al. |
| 6,544,253 B1 | 4/2003 | Tanner |
| 6,562,051 B1 | 5/2003 | Bolduc et al. |
| 6,592,593 B1 | 7/2003 | Parodi et al. |
| 6,652,572 B2 | 11/2003 | Kugler et al. |
| 6,730,119 B1 | 5/2004 | Smalling |
| 6,800,081 B2 | 10/2004 | Parodi |
| 8,685,044 B2 | 4/2014 | Bolduc et al. |
| 8,690,897 B2 | 4/2014 | Bolduc |
| 2001/0047199 A1 * | 11/2001 | Wijay .................. A61F 2/91 623/1.15 |
| 2002/0156521 A1 | 10/2002 | Ryan et al. |
| 2002/0183827 A1 | 12/2002 | Derus et al. |
| 2003/0100943 A1 | 5/2003 | Bolduc |
| 2004/0138734 A1 | 7/2004 | Chobotov et al. |
| 2004/0153143 A1 | 8/2004 | Quiachon et al. |
| 2004/0254594 A1 | 12/2004 | Alfaro |
| 2005/0070992 A1 | 3/2005 | Bolduc et al. |
| 2005/0154401 A1 | 7/2005 | Weldon et al. |
| 2005/0215874 A1 | 9/2005 | Wang et al. |
| 2006/0111692 A1 | 5/2006 | Hlavka et al. |
| 2006/0253186 A1 | 11/2006 | Bates |
| 2008/0097489 A1 | 4/2008 | Goldfarb et al. |
| 2014/0194902 A1 | 7/2014 | Bolduc et al. |
| 2014/0214051 A1 | 7/2014 | Bolduc |
| 2015/0127015 A1 | 5/2015 | Bolduc et al. |

FOREIGN PATENT DOCUMENTS

| | | |
|---|---|---|
| EP | 0 663 184 | 1/1994 |
| FR | 2299548 | 1/1975 |
| FR | 2865926 A1 | 8/2005 |
| WO | WO97/03616 | 2/1997 |
| WO | WO-9811814 A2 | 3/1998 |
| WO | WO99/53845 | 10/1999 |
| WO | WO00/16701 | 3/2000 |
| WO | WO 0016701 A1 * | 3/2000 |
| WO | WO-0160432 A1 | 8/2001 |
| WO | WO 03/032870 | 4/2003 |
| WO | WO 03/045467 | 6/2003 |
| WO | WO-03079935 A1 | 10/2003 |
| WO | WO-2004008975 A1 | 1/2004 |
| WO | WO-2005/067660 A2 | 7/2005 |
| WO | WO-2005/067660 A3 | 7/2005 |

OTHER PUBLICATIONS

"The Spiral Tracker: A New Technique for Stabilizing Prosthetic Mesh in Laparoscopic Hernia Repair", Nov. 1995 *Surgical Rounds.*
"Laparoscopic Surgery", *MedPro Month* Oct. 1995, p. 190.
"Assisted TAPP Procedure", Newman III et al., Circa 1995.
"Extraperitoneal Endoscopic Burch Repair Using a Tacker Mesh Technique", Hatchett et al., Circa 1995.
Non-Final Office Action dated Oct. 19, 2006, for U.S. Appl. No. 10/752,435, filed Jan. 6, 2004, 16 pages.

(56) References Cited

OTHER PUBLICATIONS

Final Office Action dated Jul. 12, 2007, for U.S. Appl. No. 10/752,435, filed Jan. 6, 2004, 7 pages.
Non-Final Office Action dated Mar. 18, 2008, for U.S. Appl. No. 10/752,435, filed Jan. 6, 2004, 6 pages.
Final Office Action dated Dec. 8, 2008, for U.S. Appl. No. 10/752,435, filed Jan. 6, 2004, 7 pages.
Non-Final Office Action dated Jul. 21, 2009, for U.S. Appl. No. 10/752,435, filed Jan. 6, 2004, 7 pages.
Final Office Action dated May 14, 2010, for U.S. Appl. No. 10/752,435, filed Jan. 6, 2004, 7 pages.
International Search Report dated Jan. 5, 2007, for PCT Patent Application No. PCT/US05/00059, filed Jan. 3, 2005, published on Jul. 28, 2005, as WO 2005/067660, 4 pages.
Written Opinion dated Jan. 5, 2007, for PCT Patent Application No. PCT/US05/00059, filed Jan. 3, 2005, published on Jul. 28, 2005, as WO 2005/067660, 8 pages.
International Preliminary Report on Patentability dated May 18, 2007, for PCT Patent Application No. PCT/US05/00059, filed Jan. 3, 2005, published on Jul. 28, 2005, as WO 2005/067660, 8 pages.
"U.S. Appl. No. 11/254,619, Non Final Office Action dated Jan. 6, 2014", 19 pgs.
"U.S. Appl. No. 11/488,305, Non Final Office Action dated Jan. 29, 2014", 10 pgs.
"U.S. Appl. No. 12/288,031, Response filed Nov. 15, 2013 to Non Final Office Action dated Jul. 15, 2013", 11 pgs.
"U.S. Appl. No. 12/288,034, Final Office Action dated Nov. 4, 2013", 8 pgs.
"U.S. Appl. No. 12/288,034, Response filed Feb. 4, 2014 to Final Office Action dated Nov. 4, 2013", 12 pgs.
"U.S. Appl. No. 12/917,842, Notice of Allowance dated Dec. 2, 2013", 7 pgs.
"U.S. Appl. No. 12/942,232, Response filed Jan. 9, 2014 to Non Final Office Action dated Oct. 9, 2013", 11 pgs.
"U.S. Appl. No. 13/162,384, Advisory Action dated Nov. 15, 2013", 3 pgs.
"U.S. Appl. No. 13/162,384, Response filed Oct. 18, 2013 to Final Office Action dated Aug. 27, 2013", 5 pgs.
"U.S. Appl. No. 13/495,836, Notice of Allowance dated Dec. 4, 2013", 9 pgs.
"U.S. Appl. No. 13/495,836, Response filed Nov. 5, 2013 to Non Final Office Action dated Aug. 5, 2013", 8 pgs.
"European Application Serial No. 06802580.8, Extended European Search Report dated Sep. 24, 2013", 8 pgs.
"U.S. Appl. No. 11/254,619, Final Office Action dated Jun. 19, 2014", 17 pgs.
"U.S. Appl. No. 11/254,619, Response filed May 6, 2014 to Non Final Office Action dated Jan. 6, 2014", 10 pgs.
"U.S. Appl. No. 11/488,305, Response filed Apr. 29, 2014 to Non Final Office Action dated Jan. 29, 2014", 9 pgs.
"U.S. Appl. No. 12/288,031, Final Office Action dated Mar. 12, 2014", 14 pgs.
"U.S. Appl. No. 12/288,031, Non Final Office Action dated May 10, 2012", 7 pgs.
"U.S. Appl. No. 12/288,031, Response filed Jun. 5, 2014 to Final Office Action dated Mar. 12, 2014", 15 pgs.
"U.S. Appl. No. 12/288,034, Advisory Action dated Feb. 25, 2014", 3 pgs.
"U.S. Appl. No. 12/288,034, Non Final Office Action dated May 8, 2014", 8 pgs.
"U.S. Appl. No. 12/942,232, Final Office Action dated May 22, 2014", 17 pgs.
"U.S. Appl. No. 14/210,683, Preliminary Amendment dated Mar. 24, 2014", 7 pgs.
"Australian Application Serial No. 2011224089, Response filed Mar. 21, 2014 to First Examiners Report dated Mar. 27, 2013", 74 pgs.
"Canadian Application Serial No. 2,626,403, Response filed Feb. 12, 2014 to Office Action dated Apr. 2, 2013", 20 pgs.
"European Application Serial No. 05713941.2, European Search Report dated Apr. 10, 2014", 6 pgs.
"European Application Serial No. 06802580.8, Response filed Apr. 17, 2014 to Extended European Search Report dated Sep. 24, 2013", 2 pgs.
"U.S. Appl. No. 11/254,619, Advisory Action dated Sep. 24, 2014", 3 pgs.
"U.S. Appl. No. 11/254,619, Examiner Interview Summary dated Sep. 18, 2014", 3 pgs.
"U.S. Appl. No. 11/254,619, Final Office Action dated Jun. 30, 2010", 10 pgs.
"U.S. Appl. No. 11/254,619, Final Office Action dated Oct. 20, 2011", 11 pgs.
"U.S. Appl. No. 11/254,619, Non Final Office Action dated Feb. 3, 2011", 8 pgs.
"U.S. Appl. No. 11/254,619, Non Final Office Action dated Oct. 1, 2009", 5 pgs.
"U.S. Appl. No. 11/254,619, Response filed Sep. 15, 2014 to Final Office Action dated Jun. 19, 2014", 12 pgs.
"U.S. Appl. No. 11/488,305, Final Office Action dated Aug. 14, 2014", 11 pgs.
"U.S. Appl. No. 12/288,031, Advisory Action dated Jul. 7, 2014", 4 pgs.
"U.S. Appl. No. 12/288,031, Response filed Sep. 10, 2014 to Advisory Action dated Jul. 7, 2014", 16 pgs.
"U.S. Appl. No. 12/288,034, Final Office Action dated Dec. 1, 2014", 8 pgs.
"U.S. Appl. No. 12/288,034, Response filed Aug. 1, 2014 to Non Final Office Action dated May 8, 2014", 11 pgs.
"U.S. Appl. No. 12/942,232, Advisory Action dated Aug. 7, 2014", 3 pgs.
"U.S. Appl. No. 12/942,232, Response filed Jul. 21, 2014 to Final Office Action dated May 22, 2014", 11 pgs.
"U.S. Appl. No. 13/162,384, Examiner Interview Summary dated Oct. 22, 2014", 3 pgs.
"U.S. Appl. No. 13/162,384, Non Final Office Action dated Jul. 21, 2014", 15 pgs.
"U.S. Appl. No. 13/162,384, Response filed Oct. 20, 2014 to Non Final Office Action dated Jul. 21, 2014", 12 pgs.
"European Application No. 05713941.2, Examination Notification Art. 94(3) dated Jun. 5, 2014", 7 pgs.
"U.S. Appl. No. 12/288,031, Non Final Office Action dated Feb. 17, 2015", 17 pgs.
"U.S. Appl. No. 13/162,384, Examiner Interview Summary dated Feb. 24, 2015", 1 pg.
"U.S. Appl. No. 13/162,384, Non Final Office Action dated Feb. 24, 2015", 14 pgs.
"U.S. Appl. No. 14/230,469, Non Final Office Action dated May 7, 2015", 8 pgs.
"U.S. Appl. No. 14/595,928, Preliminary Amendment filed Jan. 14, 2015", 8 pgs.
"Australian Application No. 2004287355, European Search Report dated Oct. 14, 2009", 6 pgs.
"Canadian Application No. 2,546,721, Office Action dated Aug. 31, 2010", 2 pgs.
"Canadian Application No. 2,546,721, Response filed Aug. 1, 2012 to Office Action dated Feb. 25, 2011", 9 pgs.
"European Application No. 05713941.2, Response filed Dec. 22, 2014 to Examination Notification Art. 94(3) dated Jun. 5, 2014", 15 pgs.
"European Application No. 09820886.1, Extended European Search Report dated Mar. 27, 2015", 8 pgs.

* cited by examiner

PROSTHESIS SYSTEMS AND METHODS

RELATED APPLICATION

This application is a divisional of U.S. patent application Ser. No. 10/752,435, filed Jan. 6, 2004, which is a continuation-in-part of U.S. patent application Ser. No. 10/693,255, filed Oct. 24, 2003, and entitled "Multi-Lumen Prosthesis Systems and Methods," which claims the benefit of provisional U.S. patent application Ser. No. 60/489,011, filed Jul. 21, 2003, and entitled "Bifurcated Prosthesis Systems and Methods" and which is also a continuation-in-part of co-pending U.S. patent application Ser. No. 10/271,334, filed Oct. 15, 2002, entitled "Endovascular Aneurysm Repair System," which claims the benefit of U.S. Provisional Patent Application Ser. No. 60/333,937, filed Nov. 28, 2001.

FIELD OF THE INVENTION

The invention relates generally to prostheses, and in particular, to prostheses used in the repair of diseased and/or damaged sections of a hollow body organ and/or a blood vessel.

BACKGROUND OF THE INVENTION

The weakening of a vessel wall from damage or disease can lead to vessel dilatation and the formation of an aneurysm. Left untreated, an aneurysm can grow in size and may eventually rupture.

For example, aneurysms of the aorta primarily occur in abdominal region, usually in the infrarenal area between the renal arteries and the aortic bifurcation. Aneurysms can also occur in the thoracic region between the aortic arch and renal arteries. The rupture of an aortic aneurysm results in massive hemorrhaging and has a high rate of mortality.

Open surgical replacement of a diseased or damaged section of vessel can eliminate the risk of vessel rupture. In this procedure, the diseased or damaged section of vessel is removed and a prosthetic graft, made either in a straight of bifurcated configuration, is installed and then permanently attached and sealed to the ends of the native vessel by suture. The prosthetic grafts for these procedures are usually unsupported woven tubes and are typically made from polyester, ePTFE or other suitable materials. The grafts are longitudinally unsupported so they can accommodate changes in the morphology of the aneurysm and native vessel. However, these procedures require a large surgical incision and have a high rate of morbidity and mortality. In addition, many patients are unsuitable for this type of major surgery due to other co-morbidities.

Endovascular aneurysm repair has been introduced to overcome the problems associated with open surgical repair. The aneurysm is bridged with a vascular prosthesis, which is placed intraluminally. Typically these prosthetic grafts for aortic aneurysms are delivered collapsed on a catheter through the femoral artery. These grafts are usually designed with a fabric material attached to a metallic scaffolding (stent) structure, which expands or is expanded to contact the internal diameter of the vessel. Unlike open surgical aneurysm repair, intraluminally deployed grafts are not sutured to the native vessel, but rely on either barbs extending from the stent, which penetrate into the native vessel during deployment, or the radial expansion force of the stent itself is utilized to hold the graft in position. These graft attachment means do not provide the same level of attachment when compared to suture and can damage the native vessel upon deployment.

SUMMARY OF THE INVENTION

The invention provides apparatus and methods for repairing diseased and/or damaged sections of a hollow body organ and/or a blood vessel.

One aspect of the invention provides systems and methods that include a first prosthesis and a second prosthesis. Each prosthesis includes a prosthetic material and a scaffold that supports the prosthetic material. The first prosthesis has a proximal neck region, and the second prosthesis has an end region. The end region is sized and configured to telescopically fit with the proximal neck region to form a composite prosthesis. The systems and methods manipulate a fastener attachment assembly to implant at least one fastener to secure the composite prosthesis in the tissue region.

Other features and advantages of the invention shall be apparent based upon the accompanying description, drawings, and claims.

BRIEF DESCRIPTION OF THE DRAWINGS

The invention will be understood from the following detailed description of preferred embodiments, taken in conjunction with the accompanying drawings, wherein.

DETAILED DESCRIPTION OF THE INVENTION

I. Tissue Reinforcement Prosthesis

A. Structure

Figure 1:
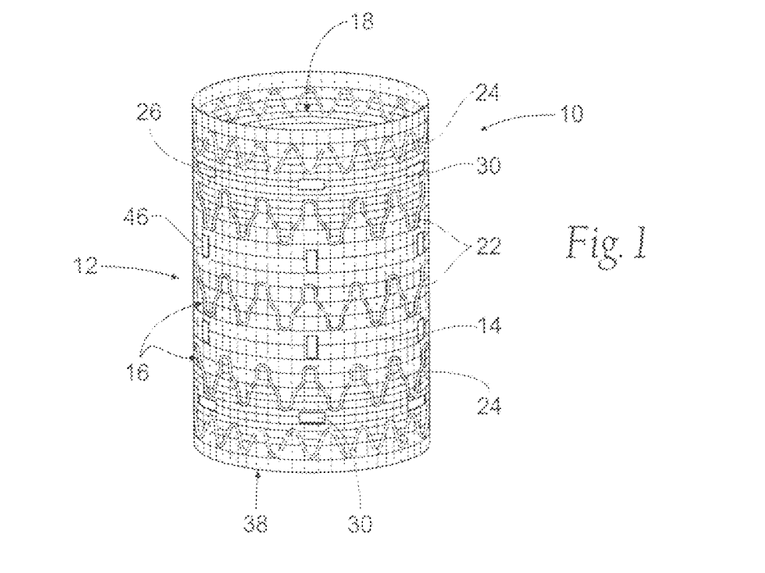
FIG. 1 is a perspective view of a tissue reinforcement prosthesis having a fastening region that accommodates the introduction of one or more fasteners.
Figure 2:
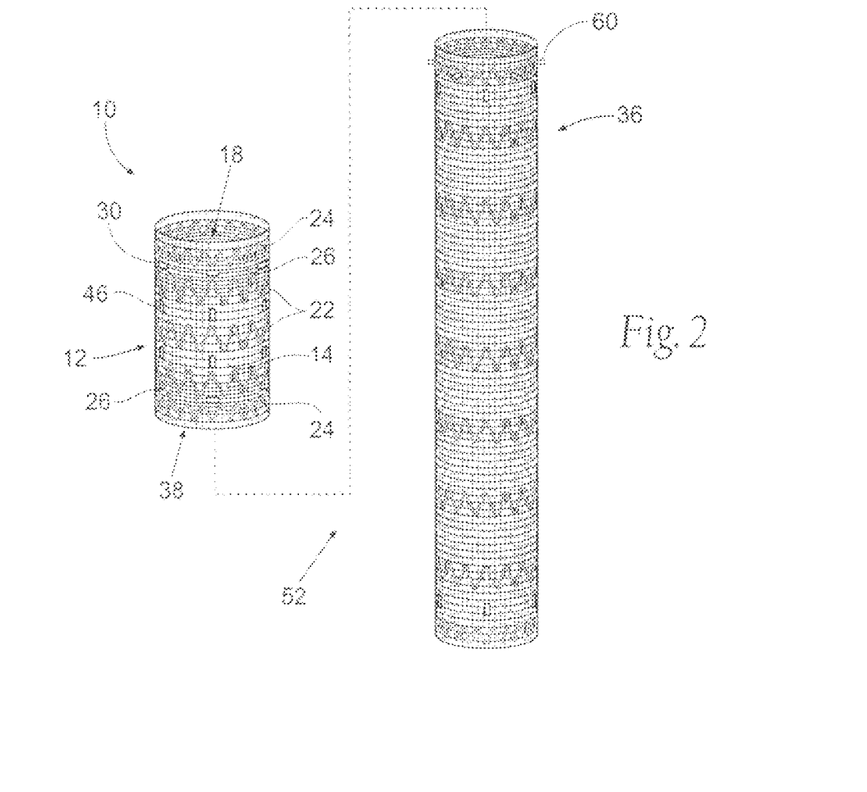
FIG. 2 is a perspective view of a prosthesis system that includes the tissue reinforcement prosthesis shown in FIG. 1 and an auxiliary prosthesis that, in use, is telescopically anchored and supported by the tissue reinforcement prosthesis.

FIG. 1 shows a tissue reinforcement prosthesis 10 that embodies features of the invention. The prosthesis 10 serves to reinforce a region of a vessel wall or hollow body organ which has been weakened by disease or damage. As will be described in greater detail later, the prosthesis 10 desirable provides a platform on which to deploy a second prosthesis 36 (see FIG. 2) in the vessel or hollow body organ. In this arrangement, the reinforcement prosthesis 10 comprises a component part of an overall prosthesis system 52.

In the illustrated embodiment (see FIG. 1), the prosthesis 10 comprises a tubular trunk 12. The trunk 12 is sized and configured to fit within a targeted region of a hollow body organ and/or a blood vessel. The targeted region is selected on the basis of certain anatomic characteristics. These characteristics include a weakened conditioned caused, e.g., by disease or damage.

The trunk 12 forms a generally cylindrical structure with an open interior lumen 18. The trunk 12 fortifies the body organ or blood vessel in the targeted region, to keep it from collapsing.

In the illustrated embodiment, the trunk 12 includes a prosthetic material 14 supported by a scaffold 16. The prosthetic material 14 is selected on the basis of its biocompatibility, durability, and flexible mechanical properties. The material 14 can comprise, e.g., woven polyester. Alternatively, a material comprising ePTFE can be used.

The scaffold 16 is desirable sized and configured to permit non-invasive deployment of the prosthesis 10 by an intravascular catheter. With this criteria in mind, the scaffold 16 is sized and configured to assume a compressed or collapsed, low profile condition, to permit its intra-vascular introduction into the hollow body organ and/or blood vessel by a catheter, as will be described in greater detail later.

Also with this criteria in mind, the scaffold 16 is sized and configured for expansion in situ from its collapsed condition into an expanded condition in contact with tissue in the targeted region, as will also be described in greater detail later.

In this respect, the scaffold 16 can comprise, e.g., a malleable plastic or metal material that expands in the presence of an applied force. In this arrangement, the deployment catheter can include, e.g., an expandable body, such as a balloon, to apply the expansion force to the scaffold 16 in situ.

Alternatively, the scaffold 16 can comprise a self-expanding plastic or metal material that can be compressed in the presence of a force, but self-expands upon removal of the compressive force. In this arrangement, the deployment catheter can include, e.g., a sleeve that can be manipulated to enclosed the scaffold 16 in a collapsed condition, thereby applying the compressive force, and to release the scaffold 16 when desired to allow the scaffold 16 to self-expand in situ.

For self-expansion, the scaffold 16 can include individual self-expanding, zigzag type main stent rings 22. The main stent rings 22 can be made, e.g., from Nitinol® wire. Still, other materials, manufacturing methods and designs can be used.

The main stent rings 22 need not be attached to one another throughout the prosthesis material 14. The individual main stent rings 22 allow for longitudinal compliance while maintaining radial support of the open interior lumen 18. This technical feature allows the prosthesis 10 to more readily accommodate changes in morphology in the targeted region. Still, it may be desirable in certain locations within the prosthesis structure to have attachments between the individual main stent rings 22 to provide enhanced stability and/or additional radial support.

Each of the main stent rings 22 can be, e.g., sewn onto prosthetic material 14. In the illustrated embodiment, in which the prosthetic material 14 is woven polyester, the attachment of the main stent rings 22 can be made, e.g., with polyester suture.

However, it is also contemplated that other attachment means could be utilized to secure the main stent rings 22 to the prosthetic material 14. These means include bonding; capturing the main stent rings 22 between two layers of prosthetic material 14; and incorporating the main stent rings 22 directly into the prosthetic material 14.

In certain locations it is desired to have the main stent rings 22 attached to the outer diameter of the prosthetic material 14. Still, it is also contemplated that the main stent rings 22 could be attached to the inner diameter of the prosthetic material 22.

At least one end of the trunk 12 desirably also includes one or more end stent rings 24. The principal purpose of an end stent ring 24 is to provide a seal between the trunk 12 and adjoining tissue. This sealing function is particularly desirable when the prosthesis 10 is deployed in a blood vessel or other body organ, where body fluids are intended to reside or pass through the prosthesis 10. The end sent rings 24 can also serve, with the main stent rings 22, to help maintain the position of the prosthesis 10 in the targeted region.

Since the end stent rings 24 desirably serve more of a sealing function than a retention function, the end stent rings 24 are desirably more compliant than the main stent rings 22. The end stent rings 24 also desirably occupy a minimum of area on the trunk 12.

The trunk 12 (material 14 and/or scaffold 16) can carry radiopaque markers 46 to help fluoroscopically position the prosthesis 10. The markers 46 can take the form, e.g. of marker bands, tight wound coils, or wire made from radiopaque materials such as platinum, platinum/iridium, or gold.

Figure 3:
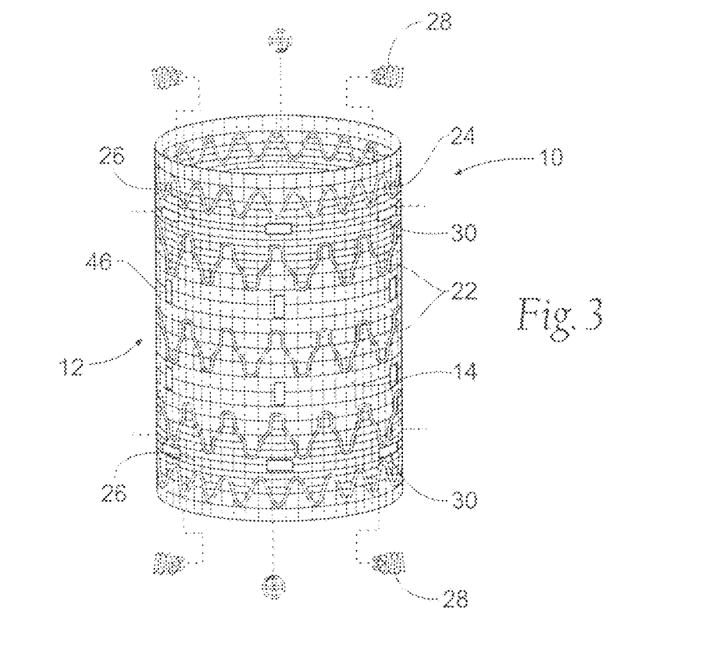
FIG. 3 is a perspective view of the tissue reinforcement prosthesis shown in FIG. 1, showing the attachment of fasteners in the fastening region.

The trunk 12 also desirably includes at least one fastening region 26 that accommodates the introduction of one or more fasteners 28 to anchor the prosthesis 10 in place (see FIG. 3). It is desirable that this region 26 of the trunk 12 be specially sized and configured for the receipt and retention of fasteners 28. For example, the size and spacing of ring stent patterns can be configured in the region 26 to specially accommodate the placement of fasteners; and/or woven fibers with an "X-pattern" or a "sinusoidal pattern" can be used in the region 26 to specially accommodate placement of fasteners; and/or the prosthetic material 14 can be folded-over to form multiple layers, to reinforce the prosthesis in the region 26 where fasteners are placed; and/or denser weave patterns or stronger fibers can be used, selected from, e.g., Kevlar™ material or Vectran™ material or metallic wire woven alone or interwoven with typical polyester fibers in the region 26 were fasteners are placed. It may also be desirable to fluoroscopically indicate this region 26 with auxiliary radiopaque markers 30 on the prosthetic material 14, and/or auxiliary stent rings 32 to aid in positioning the fasteners.

The fasteners 28 can be variously constructed. They can, e.g., comprise helical fasteners or staples.

Desirably, like the prosthesis 10 itself, the fasteners 28 are introduced by an intra-vascular fastener attachment assembly. Details of a fastener attachment assembly that deploys helical fasteners can be found in U.S. patent application Ser. No. 10/307,226, filed Nov. 29, 2002, which is incorporated herein by reference.

B. Use of the Tissue Reinforcement Prosthesis

Figure 4:
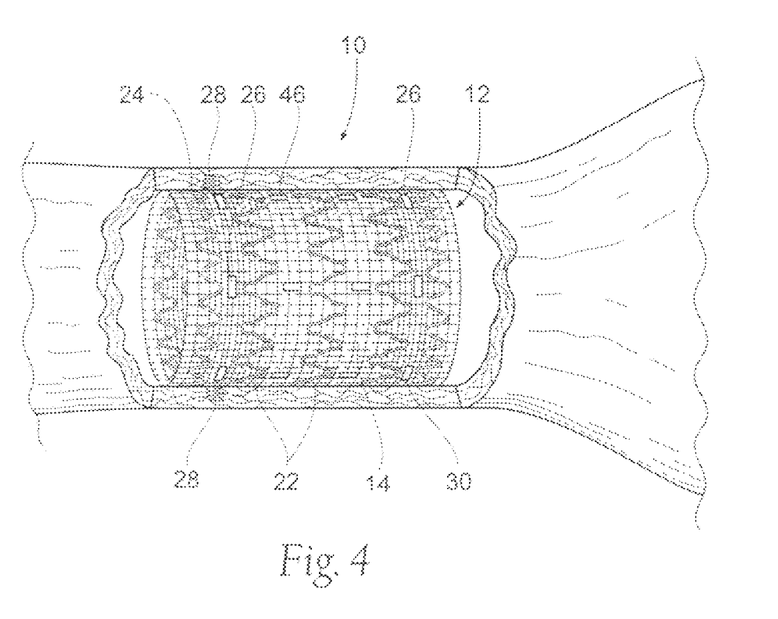
FIG. 4 is a perspective view of the tissue reinforcement prosthesis shown in FIG. 1 positioned within a hollow body organ by use of fasteners.

The targeted region for deployment of the tissue reinforcement prosthesis 10 as just described can vary. For example, the targeted region can comprise a damaged or weakened area within a given body organ, as FIG. 4 shows. In this embodiment, the presence of prosthesis 10 provides reinforcement to the body organ where damage or weakness exists.

Figure 5A:
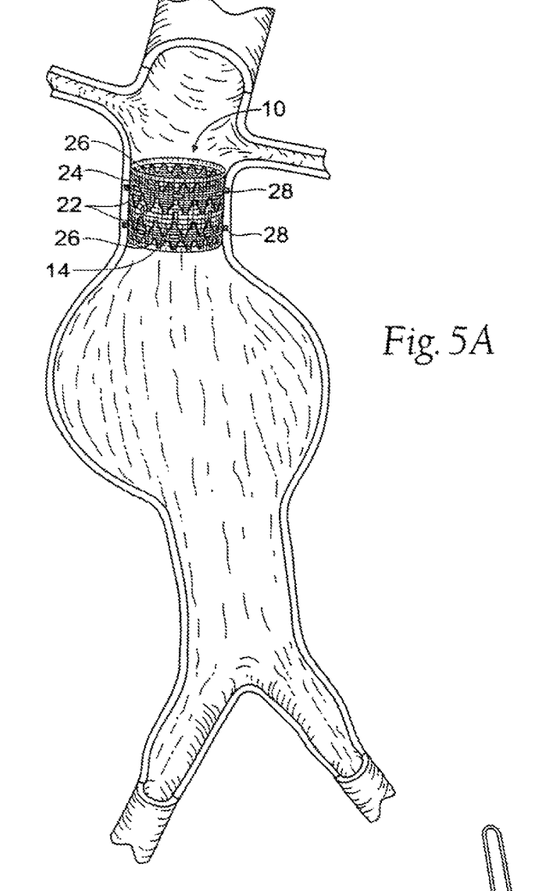
FIG. 5A is a perspective view of the tissue reinforcement prosthesis shown in FIG. 1 positioned within the proximal neck of an abdominal aortic aneurysm.

As another example (see FIG. 5A), the targeted region can comprise an aorta with an aneurysm. The use of a tissue reinforcement prosthesis 10 in this targeted region could be indicated, e.g., when the neck proximal to the aneurysm (i.e., closest to the head) is either too short or otherwise has a native anatomic feature that interferes with the secure placement of a conventional endovascular prosthesis to bridge the aneurysm. In this embodiment, the presence of prosthesis 10 provides reinforcement to the proximal neck of the aneurysmal aorta adjacent the renal arteries.

Figure 6A:
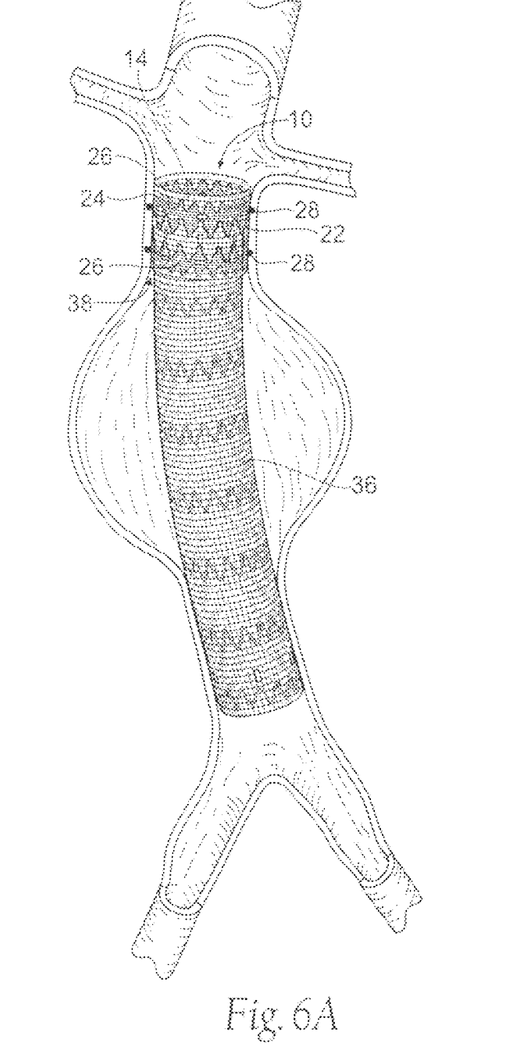
FIG. 6A is a perspective view of a prosthesis system that includes the tissue reinforcement prosthesis shown in FIG. 5A positioned within a proximal neck of the abdominal aortic aneurysm and an auxiliary prosthesis that is telescopically anchored and supported by the tissue reinforcement prosthesis and that bridges the aneurysm.

When used for this purpose (see FIG. 6A), the reinforcement prosthesis 10 can also serve to anchor and support an auxiliary prosthesis structure 36 that, in the absence of the reinforcement prosthesis 10, could not be deployed, due to native anatomic features of the vessel. In the illustrated embodiment, the auxiliary prosthesis structure 36 comprises an endovascular graft that, when deployed, bridges the aneurysm. Together, the reinforcement prosthesis 10 and the graft 36 form a prosthesis system 52, as shown in FIG. 6A.

Figure 6B:
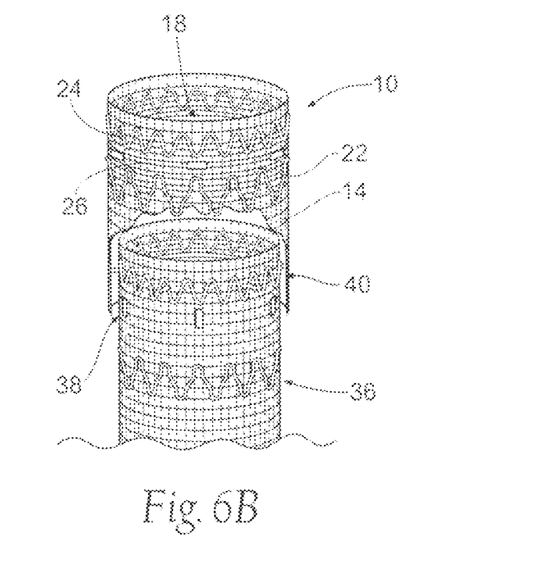
FIG. 6B is an enlarged view of the system shown in FIG. 6A, showing the telescopic fitment of the auxiliary prosthesis in the tissue reinforcement prosthesis.

In this arrangement, the graft 36 includes a proximal end 38 that is sized and configured to be telescopically fitted within the lumen 18 of the trunk 12. The lumen 18 of the trunk 12, provides an interface region or socket 40 (see FIG. 6B) that is fully enclosed within the body of the trunk 12 itself. The lumen 18 is therefore not prone to kinking or twisting or other kinds of movement independent of the trunk 12.

It is desirable that the socket region 40 of the trunk 12 be specially sized and configured for the receipt and retention of the auxiliary graft 36, e.g., by the use of folded-over materials to form multiple layers, and/or the use of denser weave patters or stronger fibers from, e.g., Kevlar™ material or Vectran™ material or metallic wire woven alone or interwoven with typical polyester fibers in the socket region 40, additional stent rings, and the like, to reinforce the prosthesis in the socket region 40 where hooks or barbs 60 of the graft 36 can obtain purchase; and/or by the use of radiopaque markers 42 to fluoroscopically identify the socket region 40 on the prosthetic material 14; and/or the use of auxiliary stent rings on the inside of the prosthetic material 14 in the socket region 40 that interfere with exterior stent rings on the graft 36, to resist migration of graft 36 from the prosthesis 10.

Being telescopically fitted within the socket region 40 (see FIG. 6B), and being also enclosed within the trunk 12 itself, the mechanical properties of the graft 36 are supplemented by the reinforcement, support, and integrity of the socket region 40 and trunk 12 themselves, and vice versa. Coupled together, the trunk 12 and the graft 36 provide enhanced resistance to migration and/or separation of the graft 36 from the trunk 12. Seated within the enclosed socket region 40, the graft 36 is peripherally sealed within the trunk 12 to resist leaks or seepage of fluids around the graft 36.

Figure 6C:
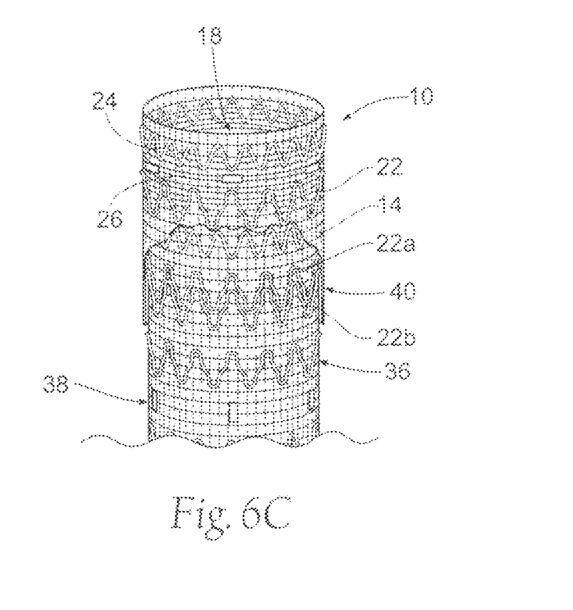
FIG. 6C is an enlarged view of the system shown in FIG. 6A, showing a telescopic, interlocking fitment of the auxiliary prosthesis in the tissue reinforcement prosthesis.

To enhance the fitment between the trunk 12 and the graft 36 within the socket region 40, a mechanically interlocking relationship can be established. For example (as shown in FIG. 6C), a supplemental main stent ring 22A on the interior of the socket region 40—which would comprise the distal-most main stent ring of the trunk 12—could be provided to mechanically engage or nest with a supplemental main stent ring 22B on the exterior of the proximal end of the auxiliary prosthesis structure 36. The mechanical interference between the supplemental stent rings 22A and 22B serves to capture the auxiliary prosthesis structure 36 within the trunk 12, preventing both distal and proximal migration between the two prostheses 10 and 36. It should also be appreciated that the inside-outside-nesting relationship in the junction between the two prostheses 10 and 36 as described can be reversed, along with the reversal of the order of deployment; that is, the auxiliary prosthesis structure 36 can be deployed first, and the prosthesis 10 deployed second to nest within an end of the auxiliary prosthesis structure 36, thereby elongating and reinforcing the neck region.

Figure 5B:
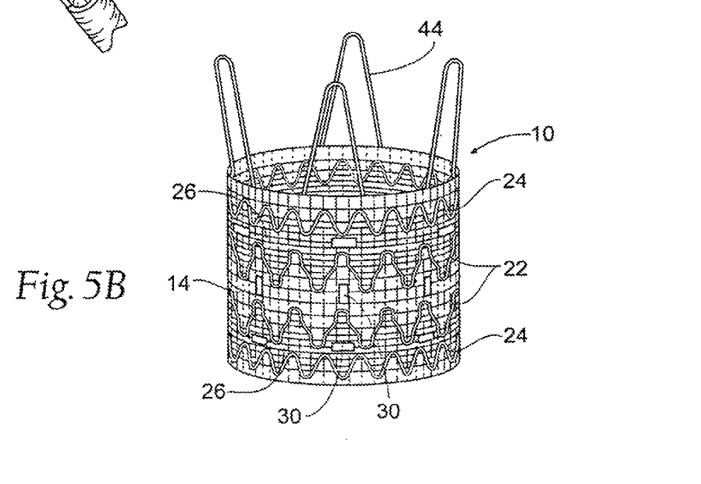
FIG. 5B is a perspective view of the tissue reinforcement prosthesis shown in FIG. 5A, with the inclusion of an optional supra-renal stent.

In this arrangement (see FIG. 5B), the trunk 12 may include a supra-renal stent 44 at its proximal end, which extends beyond the prosthetic material 14. When deployed within the aorta, this stent 44 would extend above the level of the renal arteries. The supra-renal stent 44 orients the prosthesis 10 within the lumen and aids in maintaining the position of the prosthesis 10 in the aorta without obstructing the normal blood flow into the renal arteries.

Figure 7:
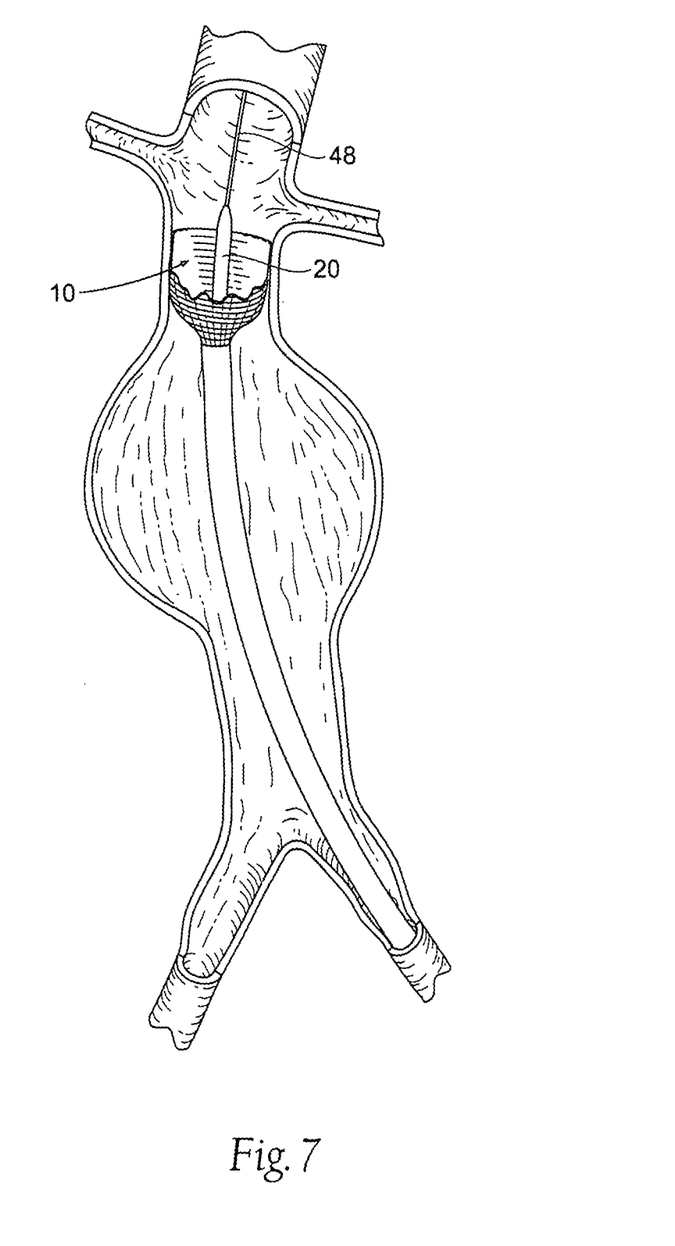
FIGS. 7, 8, and 9 are perspective views of the deployment of the system shown in FIG. 6A by the sequential use of various intra-vascular catheters, one to deploy the tissue reinforcement prosthesis (FIG. 7), another to apply fasteners to the tissue reinforcement prosthesis (FIG. 8), and another to deploy the auxiliary prosthesis (FIG. 9).

During use (see FIG. 7), a first catheter 20 is navigated over a guide wire 48 through an iliac to the desired location within the aorta near the renal arteries. The catheter 20 carries the reinforcement prosthesis 10 in a radially reduced configuration. At the targeted site, the catheter 20 releases the reinforcement prosthesis 10, which expands radially into the position shown in FIG. 5A. When the reinforcement prosthesis 10 ultimately serves to anchor an auxiliary graft 36, the trunk 12 of the prosthesis 10 desirable extends distally from the proximal neck and partially into the aneurysm sac.

Figure 8:
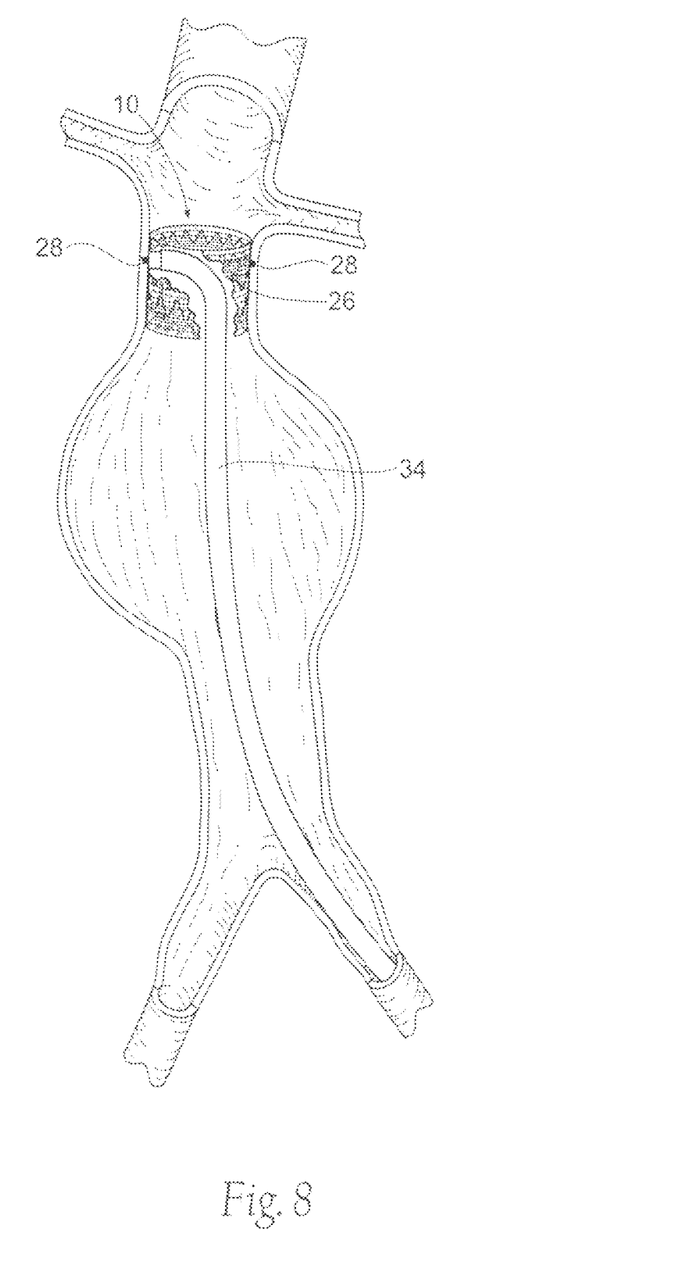

A fastener assembly 34 is next deployed (see FIG. 8) to place fasteners 28 into the end region 28 of the trunk 12. The prosthesis 10 is thereby secured in position.

Figure 9:
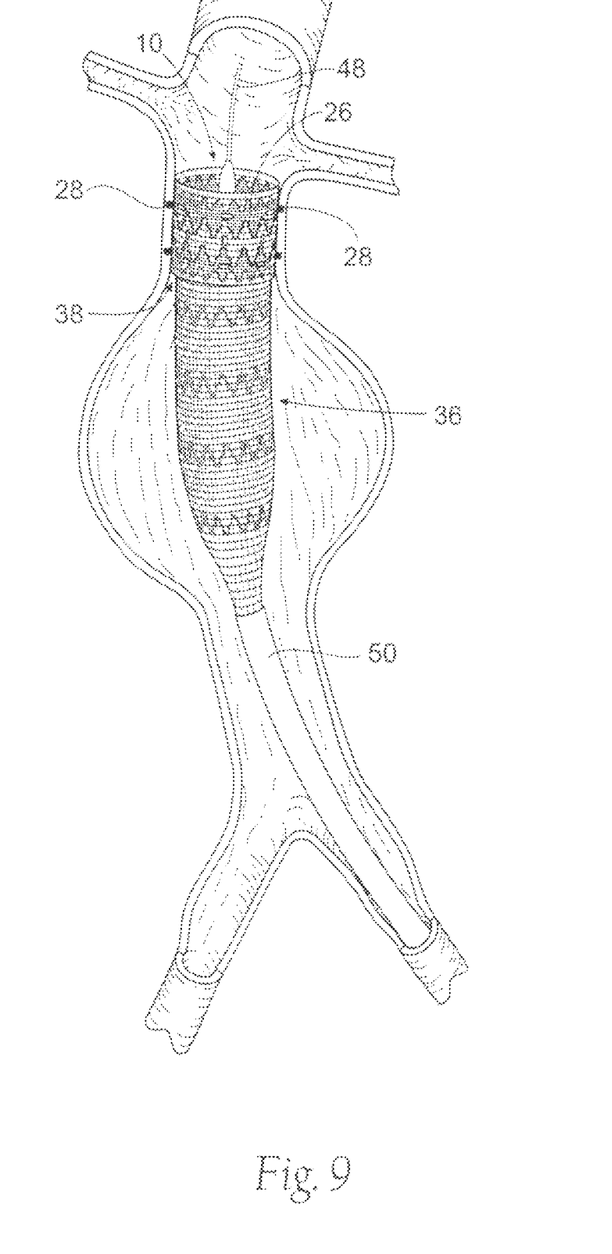

The auxiliary graft 36 is carried in a radially compressed condition by another over-the-wire catheter 50 (see FIG. 9). The catheter 50 deploys the graft 36, such that the proximal end of the graft 36 is telescopically received within the socket region 40 of the trunk 12. The prosthesis system 52 is thereby formed.

II. Other Prostheses

A. Tubular Prosthesis for General Use

Figure 10:
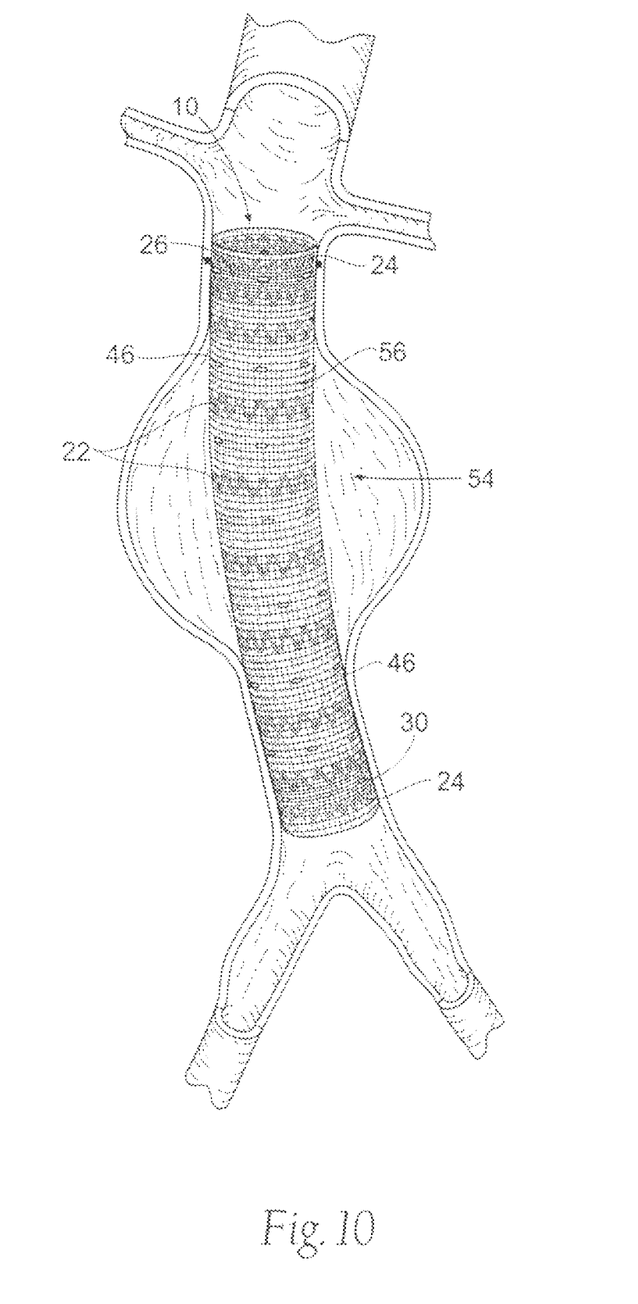
FIG. 10 is a perspective view of prosthesis positioned within an abdominal aortic aneurysm, the prosthesis having a fastening region that accommodates the introduction of one or more fasteners.

Any given tubular prosthesis 54 (see FIG. 10) can include a trunk 56 having a region 26 that is specially sized and configured for the receipt and retention of fasteners 28, in the ways previously described. In FIG. 10, the trunk 56 is sized and configured to extend, for purposes of illustration, in the aorta adjacent the renal arteries distally to a location proximal the natural bifurcation of the iliac arteries. As shown in FIG. 10, the region 26 is located in the neck of the aorta adjacent to the renal arteries. The features of the region 26, previously described, make possible the secure attachment of the prosthesis 54, without migration.

The prosthesis 54 desirable also includes other features of the prosthesis 10 already described, e.g., the main stent rings 22, the end stent rings 24, and the radiopaque markers 46. The prosthesis 54 can also include a supra-renal stent 44 of the type shown in FIG. 5B.

B. Aorta Iliac Prosthesis

Figure 11:
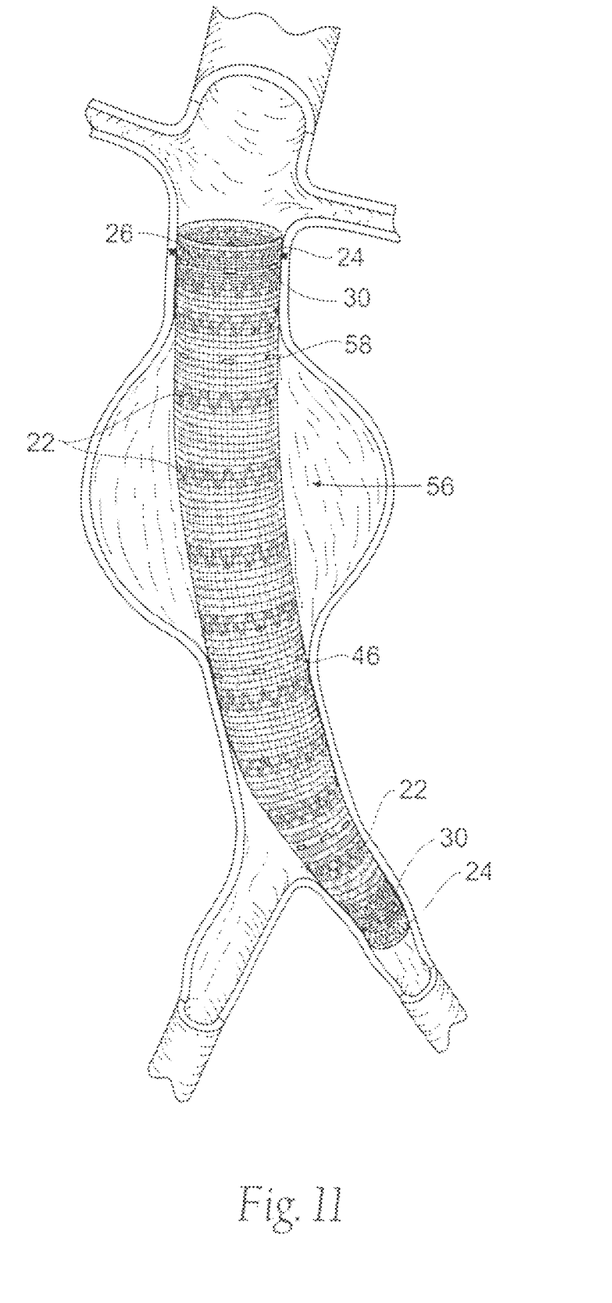
FIG. 11 is a perspective view of prosthesis positioned within an abdominal aortic aneurysm, the prosthesis having a tapered trunk located, at its proximal end, within the aorta and, at its distal end, in an iliac, the prosthesis also having a fastening region that accommodates the introduction of one or more fasteners.

As shown in FIG. 11, the trunk 58 of a given prosthesis 56 may be tapered, changing diameter from the proximal region to the distal region. In the embodiment shown in FIG. 11, the taper reduces the diameter of the trunk 58 in the proximal to distal direction. This taper direction is well suited for placement of the prosthesis 56, at its proximal end, in the aorta adjacent the renal arteries and, at its distal end, in an iliac artery, as FIG. 11 shows.

The trunk 58 of the prosthesis 56 desirable also includes a region 26 that is specially sized and configured for the receipt and retention of fasteners 28, in the ways previously described. As shown in FIG. 11, the region 26 is located in the neck of the aorta adjacent to the renal arteries. The features of the region 26, previously described, make possible the secure attachment of the prosthesis 56, without migration.

The prosthesis 56 desirable also includes other features of the prosthesis 10 already described, e.g., the main stent rings 22, the end stent rings 24, and the radiopaque markers 46. The prosthesis 54 can also include a supra-renal stent 44 of the type shown in FIG. 5B.

As described with respect to FIGS. 10 and 11, the targeted site of deployment is within the aorta adjacent the renal arteries. However, this targeted site of deployment is selected for purposes of illustrating the features of the prostheses 54 and 56, and is not intended to be limiting.

The preferred embodiments of the invention are described above in detail for the purpose of setting forth a complete disclosure and for the sake of explanation and clarity. Those skilled in the art will envision other modifications within the scope and sprit of the present disclosure.

The above described embodiments of this invention are merely descriptive of its principles and are not to be limited. The scope of this invention instead shall be determined from the scope of the following claims, including their equivalents.

We claim:

1. A system comprising:
   a first prosthesis for a hollow body organ comprising a trunk including a prosthetic material and a scaffold that supports the prosthetic material, the trunk including a neck region comprising a first stent ring;
   a second prosthesis for a hollow body organ capable of being deployed separately and sequentially to the first prosthesis, the second prosthesis comprising a prosthetic material and a scaffold that supports the prosthetic material, the second prosthesis including an end region comprising a second stent ring, the end region being sized and configured to circumferentially and telescopically fit a portion of the neck region to form a composite prosthesis;
   at least one fastener implantable into tissue by an external fastener attachment assembly to secure the composite prosthesis; and
   at least a portion of the second stent ring is configured to nest within and engage through mechanical interference at least a portion of the first stent ring to prevent distal and proximal migration between the first prosthesis and the second prosthesis.

2. A system according to claim 1, wherein the scaffold of at least one of the first and second prostheses includes self-expanding material.

3. A system according to claim 1, wherein the scaffold of at least one of the first and second prostheses includes a malleable material.

4. A system according to claim 1, wherein the at least fastener comprises a helical fastener.

5. A method for deploying a prosthesis in a tissue region in a hollow body organ comprising:
   providing a first prosthesis comprising a trunk including a prosthetic material and a scaffold that supports the prosthetic material, the trunk including a neck region;
   providing a second prosthesis capable of being deployed separately and sequentially to the first prosthesis, the second prosthesis comprising a prosthetic material and a scaffold that supports the prosthetic material, the second prosthesis including an end region that is sized and configured to circumferentially and telescopically fit a portion of the neck region to form a composite prosthesis;
   nesting and engaging through mechanical interference at least a portion of a second stent of the second prosthesis within a first stent of the first prosthesis to prevent distal and proximal migration between the first prosthesis and the second prosthesis,
   providing a fastener attachment assembly;
   deploying the first and second prostheses to the tissue region in the hollow body organ;
   telescopically fitting the end region and the neck region with one another to form the composite prosthesis; and
   manipulating the fastener attachment assembly to implant at least one fastener into tissue to secure the composite prosthesis in the tissue region.

6. A method according to claim 5, wherein the scaffold of at least one of the first and second prostheses includes self-expanding material.

7. A method according to claim 5, wherein the scaffold of at least one of the first and second prostheses includes a malleable material.

8. A method according to claim 5, wherein the at least one fastener comprises a helical fastener.

9. A method for deploying a prosthesis in a tissue region in a blood vessel, the method comprising:
   providing a first prosthesis comprising a trunk including a prosthetic material and a scaffold that supports the prosthetic material, the trunk including a distal region with a first stent ring;
   providing a second prosthesis capable of being deployed separately and sequentially to the first prosthesis, the second prosthesis comprising a prosthetic material and a scaffold that supports the prosthetic material, the second prosthesis including a proximal region that is sized and configured to telescopically fit within a portion of the distal region to form a composite prosthesis and a proximal region with a second stent ring;
   providing a fastener attachment assembly;
   deploying the first and second prostheses to the tissue region in a blood vessel, the distal region of the first prosthesis being arranged adjacent a proximal neck of an aneurysm in the blood vessel;

telescopically fitting the proximal region of the second prosthesis and the distal region of the first prosthesis to form the composite prosthesis;

nesting at least a portion of the second stent ring within at least a portion of the first stent ring to engage through mechanical interference the first stent ring and the second stent ring to prevent distal and proximal migration between the first prosthesis and the second prosthesis; and manipulating the fastener attachment assembly to implant at least one fastener into tissue to secure the composite prosthesis in the tissue region.

10. A method according to claim 9, wherein the scaffold of at least one of the first and second prostheses includes self-expanding material.

11. A method according to claim 9, wherein the scaffold of at least one of the first and second prostheses includes a malleable material.

12. A method according to claim 9, wherein the at least one fastener comprises a helical fastener.

13. A system according to claim 1, wherein the first stent ring is arranged on an interior of the neck region of the first prosthesis and the second stent ring is arranged on an exterior of the end region of the second prosthesis.

14. A system according to claim 1, wherein the first stent ring is arranged on an exterior of the neck region of the first prosthesis and the second stent ring is arranged on an interior of the end region of the second prosthesis.

* * * * *